United States Patent
Doisaki et al.

(10) Patent No.: US 8,722,104 B2
(45) Date of Patent: May 13, 2014

(54) COMPOSITION CONTAINING ORGANIC SUBSTANCE HAVING DOUBLE BOND WITH IMPROVED OXIDATIVE STABILITY

(75) Inventors: Nobushige Doisaki, Hachioji (JP); Tsuyoshi Koriyama, Hachioji (JP); Jun Okano, Hachioji (JP); Shuji Jinno, Hachioji (JP)

(73) Assignee: Nippon Suisan Kaisha, Ltd., Tokyo (JP)

( * ) Notice: Subject to any disclaimer, the term of this patent is extended or adjusted under 35 U.S.C. 154(b) by 780 days.

(21) Appl. No.: 10/535,413

(22) PCT Filed: Nov. 21, 2003

(86) PCT No.: PCT/JP03/14877
§ 371 (c)(1), (2), (4) Date: Nov. 17, 2005

(87) PCT Pub. No.: WO2004/048496
PCT Pub. Date: Jun. 10, 2004

(65) Prior Publication Data
US 2006/0134178 A1    Jun. 22, 2006

(30) Foreign Application Priority Data
Nov. 22, 2002    (JP) ................................ 2002-339906

(51) Int. Cl.
*A61K 36/00* (2006.01)

(52) U.S. Cl.
USPC .......................................................... 424/725

(58) Field of Classification Search
None
See application file for complete search history.

(56) References Cited

U.S. PATENT DOCUMENTS

| | | | | |
|---|---|---|---|---|
| 6,235,331 B1 * | 5/2001 | Kataoka et al. | ............ | 426/330.6 |
| 6,242,479 B1 * | 6/2001 | Wechter | ........................ | 514/456 |
| 2001/0031275 A1 * | 10/2001 | Forse et al. | .................... | 424/439 |
| 2002/0156051 A1 * | 10/2002 | Kutney et al. | .................... | 514/99 |

FOREIGN PATENT DOCUMENTS

| | | | |
|---|---|---|---|
| GB | 2280449 A | * | 2/1995 |
| JP | 2-189394 | | 7/1990 |
| JP | 6-298642 | | 10/1994 |
| WO | WO02/058793 | * | 8/2002 |
| WO | WO02058793 A1 | * | 8/2002 |

OTHER PUBLICATIONS

DW ACC 2002-040630, Oct. 2001, DW US, Chavali.*
DW 1995-054394, Feb. 1995, DW, Maguire.*
DW 2003-219905, Oct. 2002, DW, Chen.*

* cited by examiner

*Primary Examiner* — Terry A McKelvey
*Assistant Examiner* — Randall Winston
(74) *Attorney, Agent, or Firm* — Westerman, Hattori, Daniels & Adrian LLP

(57) ABSTRACT

To an organic substance having a double bond such as a polyunsaturated fatty acid was added an antioxidative component containing an antioxidative sesame component and ascorbic acid or an ascorbyl fatty acid ester.

The above method provides a composition containing an organic substance having a double bond exhibiting enhanced oxidative stability. Particularly, it extremely improves oxidative stability of fat and oil which contains polyunsaturated fatty acid. General-purpose refined fish oil which is easy to handle can be provided for food, medicine or feed uses.

19 Claims, 8 Drawing Sheets

COMPOSITION CONTAINING ORGANIC SUBSTANCE HAVING DOUBLE BOND WITH IMPROVED OXIDATIVE STABILITY

TECHNICAL FIELD

The present invention relates to a composition containing an organic substance having a double bond with improved oxidative stability. More specifically, the present invention relates to a composition with improved oxidative stability that is prepared by adding an antioxidative sesame component and ascorbic acid or an ascorbyl fatty acid ester as antioxidants to an easily oxidizable organic substance having a double bond, such as a polyunsaturated fatty acid.

In the present invention, the polyunsaturated fatty acid refers to a fatty acid having at least three double bonds.

BACKGROUND ART

It has recently become known that oils and fats, particularly those containing polyunsaturated fatty acids, have physiologic activity. Accordingly, such oils and fats have been increasingly and widely used in food and animal feed as additives, from the viewpoint of health. Eicosapentaenoic acid and docosahexaenoic acid are polyunsaturated fatty acids mainly contained in fish oil. It has been found that they have the effect of, for example, preventing hyperlipemia, high blood pressure, skin aging, and the like, and they have been used in medical drugs and food with health-promoting benefits. Unfortunately, oils and fats containing such a polyunsaturated fatty acid have low oxidative stability. Accordingly, food to which such an oil or fat can be added is limited, or if added to food or the like, the oil or fat undesirably generates an odor due to its oxidation, even slight oxidation. How the oil or fat is handled needs to be taken into account. For example, refined fish oil remaining after use must be hermetically sealed with the can of the fish oil filled with nitrogen gas. Thus, there are limits in use, such as of product type, distribution temperature, content, and storage conditions.

Since, for example, docosahexaenoic acid and eicosapentaenoic acid play an important role to develop the brain and retinas and the memory and learning function of babies and breast milk contains these fatty acids, modified milk for babies to which fish oil containing docosahexaenoic acid and eicosapentaenoic acid has been added is commercially available. Also, since arachidonic acid plays an important role for growth and is contained in breast milk, addition of arachidonic acid to the modified baby milk has been attempted. However, it is necessary to take care not to oxidize polyunsaturated fatty acids when these polyunsaturated fatty acids are blended into the modified baby milk. Otherwise, oxidized odor is generated by oxidation, so that not only the modified milk becomes difficult to ingest, but also the modified milk itself may be degraded to be toxic.

Encapsulated eicosapentaenoic acid ethyl esters are commercially available as medical drugs for oral administration. Refined fish oil containing eicosapentaenoic acid and docosahexaenoic acid is also available in form of capsule as health food. Since these fatty acids are liable to be oxidized, their use is limited, except for use in capsules.

In order enhance the oxidative stability, the oils and fats can be powdered. For example, oil or fat may be encapsulated into microcapsules to be powdered, or enclosed with cyclodextrin and powdered so that stable powdered oil or fat is provided. However, this approach makes the production steps complicated and decreases productivity. In addition, capsules may be broken during storage, and the type of capsule applicable for food and animal feed is limited, disadvantageously.

In order to enhance the oxidative stability of oils and fats, various types of antioxidant have been used. For example, plural types of antioxidant are used in combination, or a synergist, such as phosphoric acid, citric acid, or ascorbic acid, is added to an antioxidant to enhance the antioxidant properties. However, the oxidation stabilities of fish oils and other oils and fats having extremely low oxidative stability cannot be sufficiently enhanced by only such combinations of antioxidants and synergists.

Dibutylhydroxytoluene (BHT), butylhydroxyanisole (BHA), gallic acid, propyl gallate, tocopherols, and the like are approved as antioxidants for oils and fats and food containing oil or fat, in order to prevent oils and fats from oxidizing. In medical drugs and the like, synthetic antioxidants are used, such as BHT, BHA, TBHQ, and ethoxyquin.

Sesame oil is relatively stable to oxidation, and it has been known since a long time ago that sesame contains antioxidative components, such as sesamol and other lignans (Japanese Unexamined Patent Application Publication No. 58-132076; Shoku no Kagaku, 225 (11) pp. 40-48 (1996); Shoku no Kagaku, 225 (11) pp. 32-36 (1996)).

Sesamol is an antioxidant for oils and fats and food containing oil or fat, and is approved as a food additive. It is however reported that sesamol is not effective for oils and fats exhibiting extremely low oxidative stability, such as fish oil (NOF Corporation, from fiscal Heisei 4 (1994) to Heisei 8 (1996), DHA Koudo Seisei Chushutsu Gijutsu Kaihatsu Jigyo, Kekka Gaiyou (DHA Koudo Seisei Chushutsu Gijutsu Kenkyu Kumiai) pp. 74-79 (2002)). Sesamol is not used for enhancing the oxidative stability of fish oil.

Ascorbic acid and ascorbic acid derivatives are also approved as food additives and used as antioxidants for oils and fats and food containing oil or fat. However, they are not effective for oils and fats exhibiting extremely low oxidative stability, such as fish oil, if they are used alone, and even their combined use with tocopherol does not produce satisfactory effects.

In order to prevent the oxidation of oils and fats, combined use of various types of antioxidant has been attempted. For example, Japanese Unexamined Patent Application Publication No. 2002-142673 has disclosed a lipophilic antioxidant prepared by emulsifying gallic acid, a water-soluble antioxidant, and an oil-soluble antioxidant into a water-in-oil form with a lipophilic emulsifier. In this application, examples of the water-soluble antioxidant include vitamin C, citric acid, chlorogenic acid, their derivatives, sugar-amino reaction products, proanthocyanidin, flavone derivatives, tea extracts, grape seed extracts, and rutin, and examples of the oil-soluble antioxidant include tocopherol, ascorbyl palmitate, sesamol, and γ-oryzanol.

Effects of antioxidants have been compared for pyrolysis of tocopherol in vegetable oils in Nippon Eiyo Shokuryo Gakkaishi (Journal of Japanese Society of Nutrition and Food Science), 44 (6) pp. 493-498 (1991), 45 (3) pp. 291-295 (1992), and 45 (3) pp. 285-290 (1992). Although some of the antioxidants use sesamol and an ascorbic acid ester in combination, they do not produce effects particularly superior to other antioxidants. These literatures discuss effects in oxidation of vegetable oils (having 3 or less unsaturated bonds) at high temperatures, but not in oxidation of polyunsaturated fatty acids (having at least three unsaturated bonds) during storage at room temperature; hence different objects are used under different conditions. This is probably because the combination of sesamol and an ascorbic acid ester does not produce superior effects. In addition, the thermal instability of the antioxidants may affect antioxidant properties.

Demand for oil or fat containing an unsaturated fatty acid is increasingly growing. Accordingly, it is highly desired to solve the problem of oxidative stability, including how to handle the oil or fat, in a strict sense.

DISCLOSURE OF INVENTION

The object of the present invention is to provide an organic substance, particularly a polyunsaturated fatty acid or its ester, having a double bond with extremely improved oxidative stability.

The inventors of the present invention have conducted intensive research in order to enhance the oxidative stability of oils and fats (oils and fats containing a high proportion of polyunsaturated fatty acid, such as oils of fish and aquatic animals). As a result, the inventors found that the oxidative stability of oils and fats can be extremely enhanced by adding an antioxidative component of sesame, such as sesamol, an ascorbic acid or ascorbyl fatty acid ester in combination. In addition, the present inventors found that the antioxidant properties of antioxidative sesame component other than sesamol are also extremely enhanced by combination with ascorbic acid or ascorbyl fatty acid ester, and thus accomplished the present invention.

The main points of the present invention are the composition described in the following (1) to (13).
(1) A composition having oxidative stability comprising: an organic substance having a double bond which contains an antioxidant comprising an antioxidative sesame component and ascorbic acid or an ascorbyl fatty acid ester.
(2) A composition according to (1), wherein the double bond has active methylene, or located at the end of the organic substance.
(3) A composition according to (1), wherein the organic substance having the double bond is a polyunsaturated fatty acid or its salt or ester.
(4) A composition according to (3), wherein the polyunsaturated fatty acid contains at least one of eicosapentaenoic acid and docosahexaenoic acid.
(5) A composition according to (3 or (4), wherein the ester of the polyunsaturated fatty acid is a triglyceride containing the polyunsaturated fatty acid as a constituent, or a lower alcohol ester of the polyunsaturated fatty acid.
(6) A composition according to (3) or (4), wherein the ester of the polyunsaturated fatty acid is added in a form of refined fish oil.
(7) A composition according to any one of (1) to (6), wherein the antioxidative sesame component is at least one of the substances represented by peaks detected by high-performance liquid chromatography using an electrochemical detector at elution times of about 2.66, 3.40, 3.84, 4.57, 4.98, 5.82, 7.00, 8.67, 9.84, 11.24, 12.29, 12.49, 13.36, 14.04, 14.32, 14.74, 15.22, 15.60, 15.82, 16.34, 16.98, 18.10, 18.43, and 34.91 minutes.
(8) A composition according to any one of (1) to (6), wherein the antioxidative sesame component is extracted from sesame, sesame oil, or sesame residue, using a solvent, a lipid, or an emulsifier singly or in combination.
(9) A composition according to any one of (1) to (6), wherein the antioxidative sesame component is at least one selected from the group consisting of sesamol, sesaminol, episesaminol, pinoresinol, epipinoresinol, syringaresinol, samine, sesamolinol, and 2,3-di(4'-hydroxy-3'-methoxybenzyl)-2-buten-4-olide.
(10) A composition according to any one of (1) to (9), wherein the ascorbyl fatty acid ester contains ascorbyl palmitate or ascorbyl stearate.
(11) A composition according to any one of (1) to (10), wherein the ascorbic acid or the ascorbyl fatty acid ester is contained in an excessive amount more than the amount soluble in the polyunsaturated fatty acid or its salt or ester.
(12) A composition according to (11), wherein the excessive amount of the ascorbic acid is in a powder or solid form.
(13) A composition according to any one of (1) to (12), further comprising tocopherol.
(14) A food containing the composition as set forth in any one of (1) to (13).
(15) A powdered oil or fat containing the composition as set forth in any one of (1) to (13).
(16) A powdered baby milk containing the composition as set forth in any one of (1) to (13).
(17) A health food containing the composition as set forth in any one of (1) to (13).

ADVANTAGES

The present invention can extremely enhance the oxidative stability of a composition containing an organic substance with low oxidative stability which has a double bond having active methylene, or a double bond at its end, particularly containing a polyunsaturated fatty acid. The present invention can make easy the addition of a composition containing a polyunsaturated fatty acid to medical drugs, cosmetic preparations, food, and the like, which has been conventionally limited. Also, the content of such a composition can be increased. Since the antioxidative sesame component and ascorbic acid or an ascorbyl fatty acid ester used in the present invention have been ingested as food for a long time, a safe antioxidant can be provided for food as well.

BEST MODE FOR CARRYING OUT THE INVENTION

Figure 1:
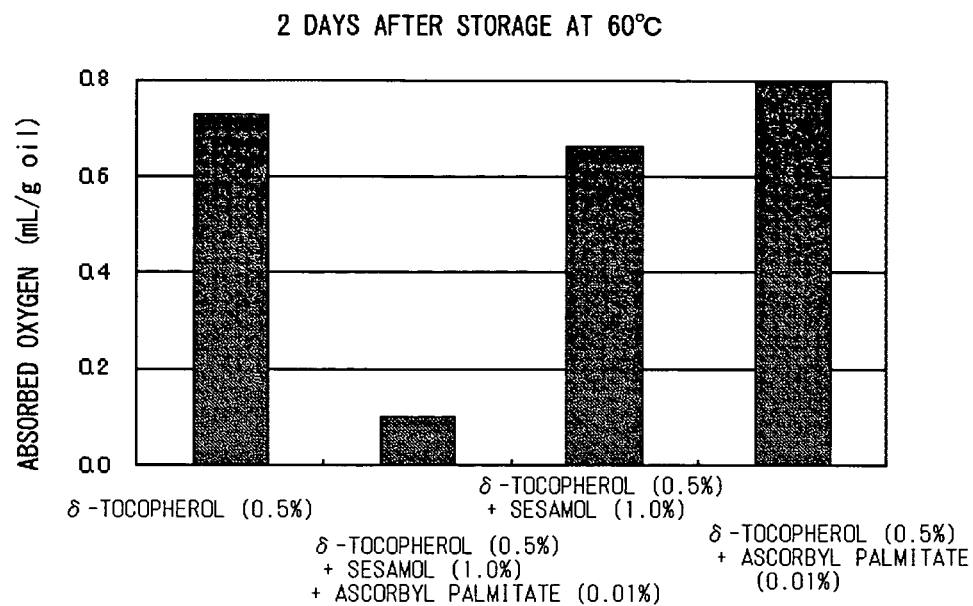
FIG. 1 shows amounts of oxygen absorbed by oil or fat in Example 1.

The organic substance having a double bond, used in the present invention is liable to naturally oxidize even under storage at room temperature. For example, the organic substance has a double bond having active methylene, or a double bond at its end. Examples of such substances include unsaturated fats and polymer materials (monomers). Among the unsaturated fats, polyunsaturated fatty acids having at least four double bonds are particularly easily oxidized, and accordingly conventionally used antioxidants cannot sufficiently prevent the oxidation.

The polyunsaturated fatty acid or its salt or ester used herein refers to a polyunsaturated fatty acid, a lower alcohol ester of the polyunsaturated fatty acid, and a triglyceride containing the polyunsaturated fatty acid as a constituent. Its examples include oils of fish and aquatic animals containing a high proportion of eicosapentaenoic acid, docosahexaenoic acid, or the like, and their esters, such as eicosapentaenoic acid ethyl ester and docosahexaenoic acid ethyl ester. The polyunsaturated fatty acid refers to a fatty acid having 3 or more double bonds. Fatty acids having 4 or more double bonds are particularly effective. Exemplary polyunsaturated fatty acids having 3 or more double bonds include α-linolenic acid, arachidonic acid, eicosapentaenoic acid, and docosahexaenoic acid. Also, polyunsaturated fatty acid-based compounds used in the present invention include esters of such fatty acids, such as methyl esters, ethyl esters, triglycerides, ditriglycerides, and monoglycerides.

Eicosapentaenoic acid is a generic name of fatty acids having a carbon number of 20 and five double bonds, and natural eicosapentaenoic acids are cis-type pentavalent straight-chain unsaturated n-3 fatty acids having double bonds at the 5, 8, 11, 14, and 17 positions. Docosahexaenoic acid is a straight-chain hexenoic acid having a carbon number of 22 and cis-double bonds at the 4, 7, 10, 13, 16, and 19 positions. These EPAs and DHAs derived from nature are contained in natural oils and fats, particularly in oils and fats of marine products, such as tuna, bonito, chub mackerel, sardine, and pacific cod. They may be present in a form of glyceride or other derivatives.

In the present invention, any material can be used as long as it results in an oil or fat containing a polyunsaturated fatty acid having 3 or more double bonds. Examples of the material for oil or fat containing the polyunsaturated fatty acid include marine fish, such as sardine, chub mackerel, saury, tuna, and bonito; and fats derived from microorganisms; crustaceans, such as euphausiid and shrimp and lobster; fish oil; animal and vegetable oils; and genetically modified vegetable oils.

The polyunsaturated fatty acid having 3 or more double bonds can be concentrated by wintering or enzymatically treating oil or fat containing the polyunsaturated fatty acid. Alternatively, the oil or fat containing a polyunsaturated fatty acid having 3 or more double bonds may be esterified with alcohol or hydrorified to fatty acid, and then subjected to distillation, urea addition, column treatment, enzymatic treatment, or supercritical carbon dioxide treatment. Thus, the polyunsaturated fatty acid can be concentrated.

The antioxidant used in the present invention does not reduce substances that have been already oxidized. It is therefore necessary that oxides be removed from the organic substance having a double bond before adding the antioxidant. For a polyunsaturated fatty acid or its salt or ester, it is also necessary to remove oxides by degumming, deacidification, decolorization, deodorization, or the like. Preferably, the organic substance is refined to a PV of 3.0 meq/kg or less and an AV of 1.0 or less, and has no odor in terms of sensory testing.

The antioxidant used in the present invention does not reduce substances that have been already oxidized. It is therefore desired the organic substance to be added has a high refining degree as much as possible by removing oxides. Since odors resulting form oxidation are generated even by slight oxidation, it is necessary to sufficiently refine the organic substance before adding the antioxidant. If refined fish oil is used, it is preferably refined to a PV of 3.0 meq/kg or less and an AV of 1.0 or less so as to be odorless in terms of sensory testing.

Oil or fat constituted of the unsaturated fatty acid contained in the composition of the present invention may be acidified by hydrolysis or oxidation. The oxidation produces hydroperoxides and decomposition products of the hydroperoxides deteriorate taste and flavor.

For example, soybean oil is oxidized to produce propionaldehyde, 2-pentenal, caproic aldehyde, acetaldehyde, and crotonaldehyde. These oxidation products from the polyunsaturated fatty acid are causes of disagreeable odors of fish oil, and thus a fishy odor peculiar to fish oil is generated. Refined oils containing the unsaturated fatty acid, such as fish oil, soybean oil, linseed oil, and rape-seed oil, may generate disagreeable odor or change in color in the very early stages of their oxidation. This phenomenon is called "Modori" (deterioration). The "Modori" phenomenon in color of decolorized refined vegetable oil is caused by an oxidation product from vitamin E, chromane-5,6-quinone. The present invention is intended to prevent the unsaturated fatty acid from oxidizing, and produces remarkable effects particularly in animal oil having a low oxidative stability.

The organic substance having a double bond, used in the present invention may be provided in form of tape, poultice, or adhesive tape that contains a medical drug using a polymer having a double bond as the base material. Accordingly, the present invention can be applied to rubber polymers, such as butadiene rubber, styrene butadiene rubber, butyl rubber, chloroprene rubber, acrylic rubber, natural rubber, isoprene rubber, and styrene-isoprene-styrene block copolymer. The composition of the present invention may be used in combination with an antioxidant generally used in these rubber polymers.

Figure 6:
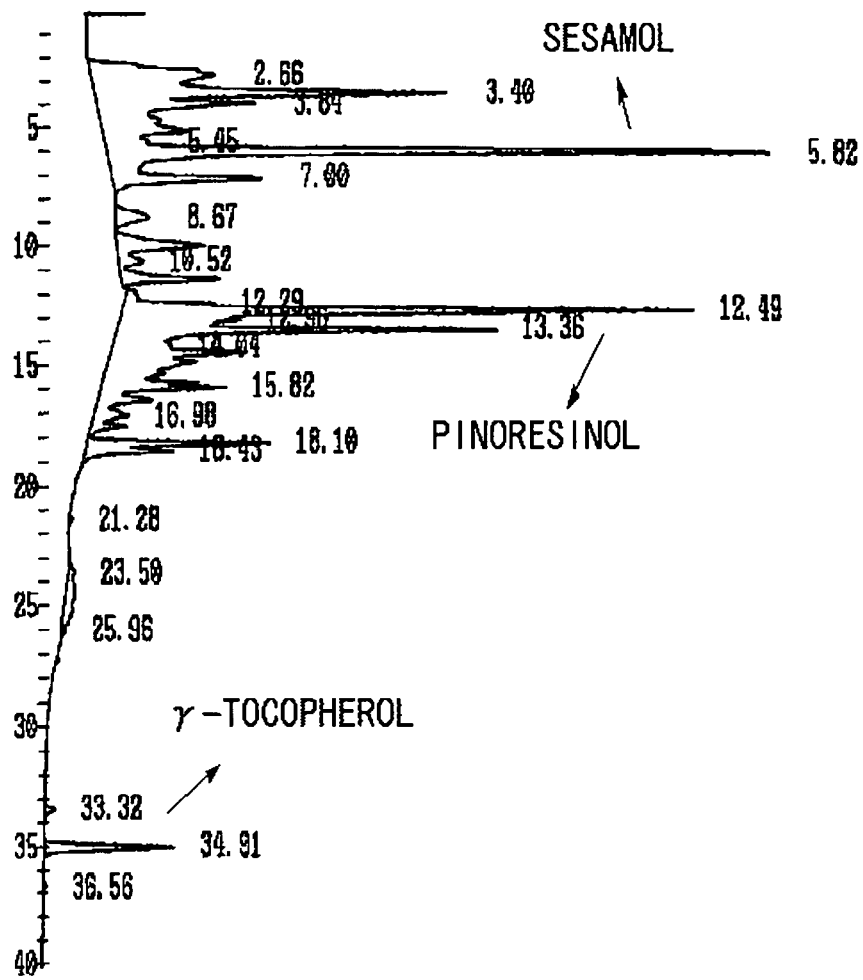
FIG. 6 is a high-performance liquid chromatographic chart of sesame residue extract 1, obtained with an electrochemical detector in Example 6.

The antioxidative sesame component used in the present invention may be of phenol form. Examples such antioxidative components include sesamol, sesaminol, episesaminol, pilsinol, epipinoresinol, syringaresinol, samine, sesamolinol, and 2,3-di(4'-hydroxy-3'-methoxybenzyl)-2-buten-4-olide. In FIG. 6, the peaks of the HPLC chart, which were detected by an electrochemical detector, represent their respective antioxidative components. This chart shows that sesame contains many antioxidative components. While these components, including sesamol, can produce a satisfactory effect independently, mixtures of these components exhibit stronger antioxidant properties. The antioxidative sesame components may be used singly or in combination.

Hence, the antioxidative sesame component used in the present invention may be highly purified antioxidative component from sesame, or a lightly purified antioxidative component including sesamol, which is also containing the other substance derived from sesame, such as sesame lignan, or tocopherol. The antioxidative sesame component may be synthesized. Furthermore, sesame oil may be used as it is, as long as there is no problem with the odor peculiar to sesame oil.

Specifically, the antioxidative component can be extracted from sesame seeds, sesame oil, or degreased sesame residue after expressing sesame oil. Alternatively, it can be obtained from scum, which is a component prepared by distillation during deodorization of sesame oil. Preferably, roasted sesame is used because the antioxidative component is increased by roasting. Since non-roasted sesame contains a certain proportion of antioxidative component, it can also be used. For extraction from sesame seeds, it is preferable that the principal constituent or neutral lipid be expressed, or removed with a nonpolar solvent, such as hexane. Although sesame oil can be used as it is, its application is limited because the absolute quantity of the neutral lipid is high and, accordingly, the antioxidative component content is low.

The sesame extract used in the present invention may be prepared by any method, as long as antioxidative components such as represented by HPLC peaks shown in FIG. 6 can be extracted. For example, the antioxidative components can be extracted by use of a solvent, a lipid, or an emulsifier. More specifically, the antioxidative components can be extracted from sesame, sesame oil, or sesame residue by use of organic solvents, such as nitrous oxide, acetone, ethanol, ethyl methyl ketone, glycerol, ethyl acetate, methyl acetate, diethyl ether, cyclohexane, dichloromethane, 1,1,1,2-tetrafluoroethane, 1,1,2-trichloroethane, carbon dioxide,1-butanol, 2-butanol, butane, 1-propanol, 2-propanol, propane, propylene glycol, hexane, and methanol; lipids, such as triglyceride, diglyceride, and monoglyceride; and emulsifiers, such as propylene glycol fatty acid esters, polyglycerol fatty acid esters, and sorbitan fatty acid esters. In addition, after removal of the solvent by evaporation, the extract is redissolved in an organic solvent. Then, water-soluble constituents are removed by partition with water, or insoluble constituents are removed by filtration. Thus, the antioxidative component can be concentrated.

In the present invention, the amount of antioxidant used in the external composition can be varied depending on the storage conditions and period or the base material used. If sesamol of sesame is used as the antioxidant, a content of 0.5% or more to the polyunsaturated fatty acid is effective. 1% or more is preferable. Although at most about 0.1% of ascorbyl fatty acid ester can be dissolved in the polyunsaturated fatty acid, it can be appropriately increased according to the application because the duration of antioxidant properties can be enhanced by adding an excessive amount of the antioxidant. For example, a composition prepared by adding 0.1% of sesamol and 0.1% of ascorbyl palmitate to refined fish oil can be preserved for 2 to 3 months at room temperature under open conditions.

Examples of the ascorbic acid or ascorbyl fatty acid ester used in the present invention include ascorbic acid and ascorbyl fatty acid esters such as ascorbyl palmitate and ascorbyl stearate. As an alternative to these materials, salts of ascorbic acid can also be used. Preferred are materials having a high solubility in lipids.

In the case of use of the ascorbic acid or ascorbyl fatty acid ester among antioxidants used in the present invention, the antioxidant properties can be further maintained by using an excessive amount of the antioxidant more than its soluble amount. Since it is considered that the antioxidant used for oil or fat is not effective unless it is dissolved, an amount of antioxidant more than saturated concentration is not generally added. However, as shown in Examples 11 and 12, the antioxidant properties can be further maintained by adding an excessive amount of ascorbic acid or an ascorbyl fatty acid ester, rather than by adding a saturated concentration. The presence of an excessive amount of ascorbic acid or ascorbyl fatty acid ester is effective even if the antioxidative sesame component is constant. The excessive amount of ascorbic acid or ascorbyl fatty acid ester is effective irrespective of whether it is in powder form or solid form. If the ascorbic acid or ascorbyl fatty acid ester is used under conditions not allowing natural diffusion, preferably, it is finely powdered and uniformly dispersed.

In addition to the antioxidative sesame component and the ascorbic acid or ascorbyl fatty acid ester, a tocopherol may be added. The tocopherol may be selected from among $\alpha$-, $\beta$-, $\gamma$-, and $\delta$-tocopherols and mixed tocopherol, but preferably $\delta$-tocopherol is used. Tocopherol is often added to commercially available polyunsaturated fatty acids and their salts and esters, such as refined fish oil, in the stage of production. Hence, use of these raw materials naturally results in a product containing tocopherol. Whether tocopherol is present or absent does not affect the synergistic effect of the antioxidative sesame component and the ascorbic acid or ascorbyl fatty acid ester.

The oil or fat whose oxidative stability has been enhanced by adding an antioxidative sesame component and ascorbic acid or an ascorbyl fatty acid ester can exhibit satisfactory oxidative stability alone, but it may be used in combination with another antioxidant. Also, it may be mixed with another oil or fat having superior oxidative stability (for example, vegetable oil). Other antioxidants include erythorbic acid, sodium erythorbate, isopropyl citrate, dibutylhydroxytoluene (BHT), and butylhydroxyanisole (BHA). Antioxidants used in combination in food include: food additives, such as tocopherols, hollyhock flower extract, Azuki extract, *aspergillus terreus* extract, calcium disodium ethylenediaminetetraacetate, disodium ethylenediaminetetraacetate, ellagic acid, erythorbic acid, sodium erythorbate, enju extract, $\gamma$-oryzanol, catechin, licorice oil extract, guajac resin, quercetin, isopropyl citrate, clove extract, enzymatically modified isoquercitrin, enzymatically modified rutin (extract), enzymatically decomposed apple extract, sesame seed oil unsaponifiable matter, rice bran oil extract, enzymatically decomposed rice bran, L-cysteine hydrochloride, dibutylhydroxytoluene, Queensland arrowroot extract, essential oil-removed fennel extract, horseradish extract, sesamoline, sage extract, dropwort extract, buckwheat extract, amino acid-sugar reaction product, tea extract, tempeh extract, dokudami extract, rape seed oil extract, coffee bean extract, nordihydroguajaretic acid, sunflower seed extract, pimento extract, ferulic acid, butylhydroxyanisole, grape seed extract, blueberry leaf extract, propolis extract, hego-ginkgo leaf extract, hesperetin, pepper extract, garden balsam extract, gallic acid, propyl gallate, melaleuca oil, morin, chinese bayberry extract, eucalyptus leaf extract, gentian root extract, enzymatically decomposed rutin, rutin (extract), and rosemary extract; and antioxidants approved in other countries, such as thiodipropionic acid, distearyl thiodipropionate, octyl gallate, dodecyl gallate, and tert-butylhydroquinone.

Since the composition of the present invention has superior oxidative stability, it can be added to various types of food. For example, skimmed milk, milk casein, milk protein, lactose, oligosaccharide, cane sugar, or dextrin is dissolved in hot water to mix, and then vitamins and minerals are dissolved in the water phase. The oil or fat of the present invention is added to the water phase and mixed with a homo-mixer or the like, followed by homogenizing with a homogenizer. The resulting emulsion is sterilized, concentrated, or spraydried in the usual manner to yield modified powder milk. Also, the composition of the present invention may be powdered oil using various types of powder base material in the same manner. If the composition is added to food, it is determined whether the composition is in oil or fat form or powdered oil form, depending on the characteristics of the food. The composition may be added to general food, or encapsulated or tableted to prepare health food or a supplement.

EXAMPLES

The present invention will be further described with reference to the following examples, but the invention is not limited to the examples.

In the examples, the following materials were used as the refined fish oil, sesamol, ascorbyl palmitate, ascorbic acid, δ-tocopherol.

Refined fish oil (containing 0.5% by weight of δ-tocopherol): DD Oil Type 3 (refined fish oil produced by refining tuna oil to a peroxide value of 5 meq/kg or less, an acid value of 1 or less, and a color Gardner of 3 or less by degumming, deacidification, deodorization, or other process), produced by Nippon Suisan Kaisha, Ltd.

Refined fish oil (not containing δ-tocopherol): taken as a sample before adding δ-tocopherol in the process of DD Oil Type 3 preparation, produced by Nippon Suisan Kaisha, Ltd.

Refined fish oil (sardine oil): DD Oil Type 2 (refined fish oil produced by refining sardine oil to a peroxide value of 5 meq/kg or less, an acid value of 1 or less, and a color Gardner of 3 or less by degumming, deacidification, deodorization, or other process; containing 28% by weight of EPA, 12% by weight of DHA, and 0.5% by weight of δ-tocopherol), produced by Nippon Suisan Kaisha, Ltd.

Sesamol: sesamol (purity: 98%) produced by Nacalai Tesque, Inc.

Ascorbyl palmitate: ascorbyl palmitate (purity: 95% or more) produced by Sankyo Foods Co. Ltd.

Ascorbic acid: L(+)-ascorbic acid (purity: 99.5%) produced by Nacalai Tesque, Inc.

δ-Tocopherol: D-δ-tocopherol (purity: 90%) produced by Wako Pure Chemical Industries Eicosapentaenoic acid ethyl ester: prepared by ethanolysis of sardine oil in the presence of metallic sodium to prepare sardine oil ethyl ester and purifying the ester by distillation and HPLC to a purity of 99%.

α-Tocopherol: (±)-α-tocopherol (purity: 98%) produced by Wako Pure Chemical Industries Example 1

<Test for Effect of Sesamol+Ascorbyl Palmitate+δ-Tocopherol>

The following antioxidant preparations were added separately to refined fish oil (containing 0.5% by weight of δ-tocopherol) to prepare samples.

sesamol (1.0% by weight)+ascorbyl palmitate (0.01% by weight)
sesamol (1.0% by weight) alone
ascorbyl palmitate (0.01% by weight) alone After 3 mL of the samples were placed separately in respective 30 mL brown bottles and hermetically sealed with septums, the samples were stored at 60° C. After 2 days, the concentration of oxygen in the headspace was measured by gas chromatography and the amount of oxygen absorbed by (reacted with) the oil was calculated. The results are shown in FIG. 1. FIG. 1 shows that the combined use of sesamol and ascorbyl palmitate in the refined fish oil reduced the amount of absorbed oxygen and much more increased the oxidative stability of the refined fish oil than the case where sesamol or ascorbyl palmitate was singly added.

Example 2

<Test for Effect of Sesamol+Ascorbic Acid+δ-Tocopherol>

Figure 2:
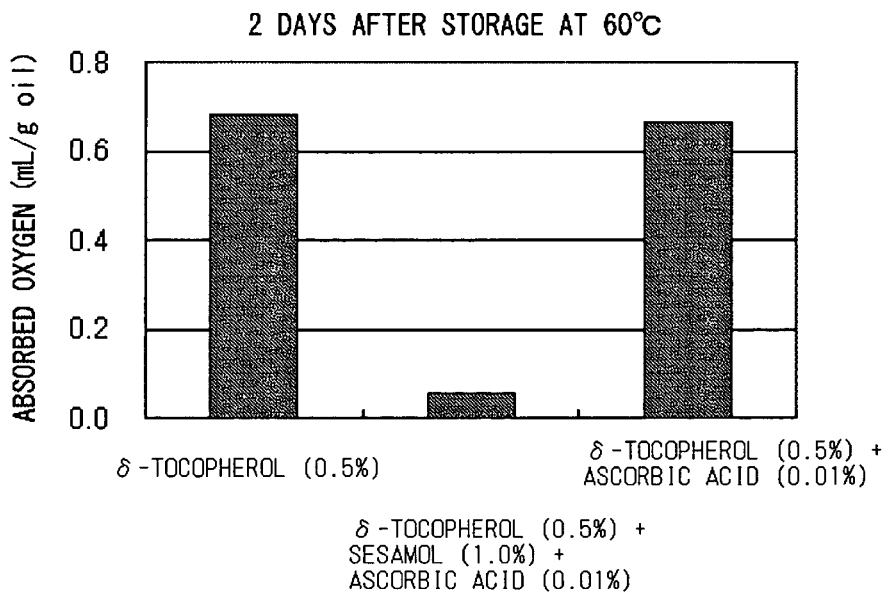
FIG. 2 shows amounts of oxygen absorbed by oil or fat in Example 2.

The following antioxidant preparations were added separately to refined fish oil (containing 0.5% by weight of δ-tocopherol) to prepare samples.

sesamol (1.0% by weight)+ascorbic acid (0.01% by weight)
ascorbic acid (0.01% by weight) alone After 4 mL of the samples were placed separately in respective 30 mL brown bottles, storage tests were performed in the same manner as in Example 1. The results are shown in FIG. 2. FIG. 2 shows that the combined use of sesamol and ascorbic acid in the refined fish oil reduced the amount of absorbed oxygen and much more increased the oxidative stability of the refined fish oil than the case where ascorbic acid was singly added.

Example 3

<Content Dependence of Sesamol and Ascorbyl Palmitate>

The antioxidant preparations constituted of δ-tocopherol, sesamol, and ascorbyl palmitate in the following proportions were added separately to refined fish oil (containing 0.5% by weight of δ-tocopherol) to prepare samples.

0.5%:0.5%:0.05%
0.5%:0.5%:0.1%
0.5%:1.0%:0.05%
0.5%:1.0%:0.1%

Figure 3:
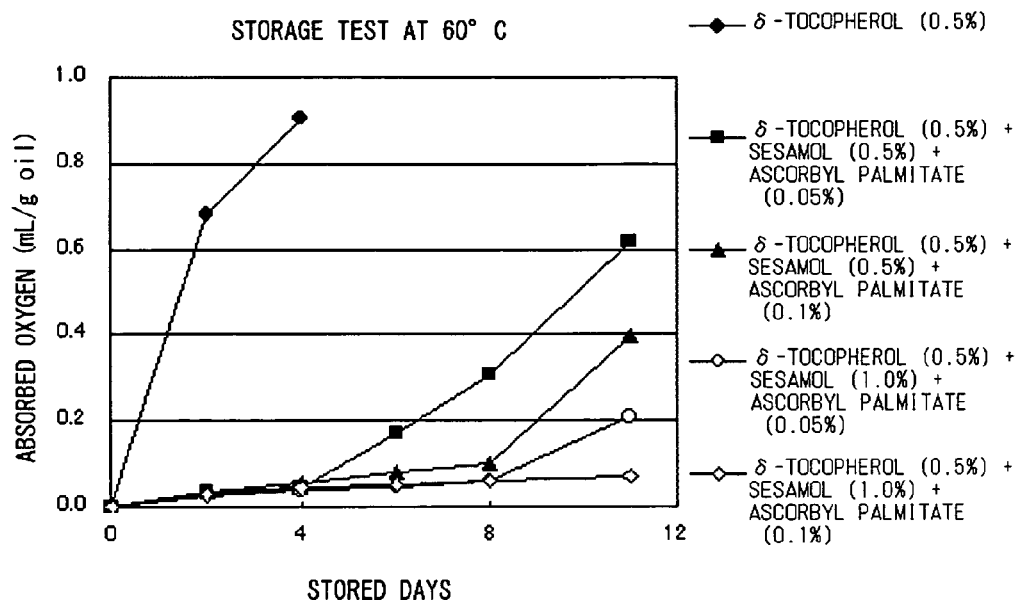
FIG. 3 shows amounts of oxygen absorbed by oil or fat in Example 3.

The samples were subjected to the same storage test as in Example 2 for 11 days. FIG. 3 shows the results. The results suggest that as the contents of sesamol and ascorbyl palmitate in the refined fish oil are increased, the amount of absorbed oxygen is reduced, and that the oxidative stability of the refined fish oil can be increased with content dependence.

Example 4

<Test for Effect of Sesamol+Ascorbyl Palmitate>

Figure 4:
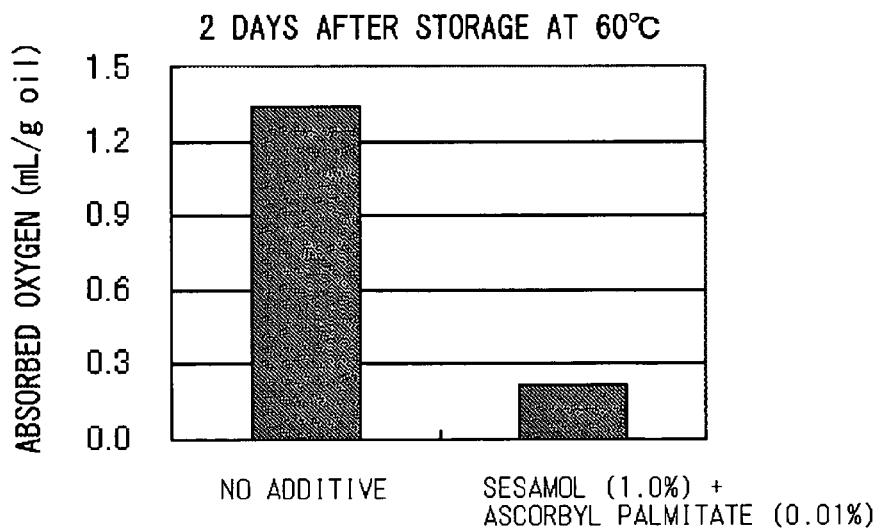
FIG. 4 shows amounts of oxygen absorbed by oil or fat in Example 4.

An antioxidant preparation of sesamol (1.0% by weight)+ascorbyl palmitate (0.01% by weight) was added to refined fish oil (not containing δ-tocopherol) to prepare a sample. The resulting sample was subjected to the same storage test as in Example 1. The results are shown in FIG. 4. It has been found that the combined used of sesamol and ascorbyl palmitate can reduce the absorption of oxygen and greatly increase the oxidative stability of the refined fish oil, without using tocopherol.

Example 5

<Test for Effect of Sesame Oil Extract+Ascorbyl Palmitate (0.1% by weight)+δ-Tocopherol>

To 8.23 g of roasted sesame oil was added 100 mL of methanol, and the mixture was strongly agitated. Then, methanol was evaporated from the methanol phase to obtain 0.28 g of extract. It was confirmed that this extract from methanol contained sesamol, by thin layer chromatography (thin layer: Kiesolgel 60 F254, 0.25 mm, produced by Merck & Co., Inc.; developing solvent:hexane:diethyl ether:acetic acid=70:30:1; coloring reagent: 1,1-diphenyl-2-picrylhydrazyl, free Radical).

Figure 5:
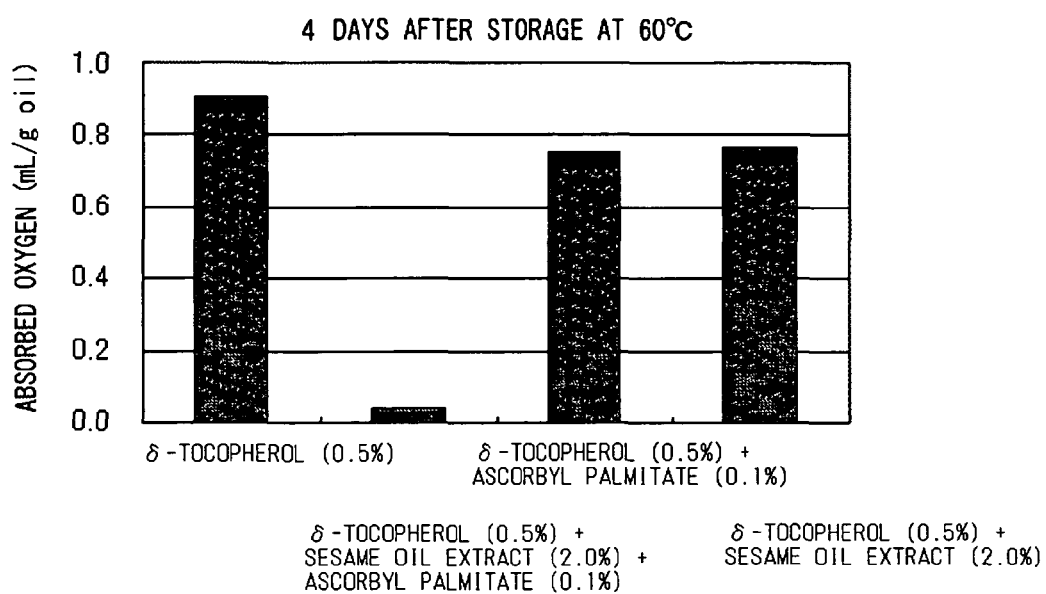
FIG. 5 shows amounts of oxygen absorbed by oil or fat in Example 5.

The following antioxidant preparations were added separately to refined fish oil (containing 0.5% by weight of δ-tocopherol) to prepare samples.

methanol extract of sesame oil (2.0% by weight)+ascorbyl palmitate (0.1% by weight)
    methanol extract of sesame oil (2.0% by weight) alone
    ascorbyl palmitate (0.1% by weight) alone The samples were subjected to the same storage test as in Example 2. The results are shown in FIG. 5. It has been found that the methanol extract of sesame oil as well as sesamol does not produce the effect by itself, and that combined use with ascorbyl palmitate reduces the amount of absorbed oxygen and increases the oxidative stability of the refined fish oil.

Example 6

<Test for Effect of Roasted Sesame residue Extract+Ascorbyl Palmitate+δ-Tocopherol>

(1) Roasted Sesame Residue Extract 1

To 1.0 kg of roasted sesame residue was added 2.0 kg of 95% ethanol, and the mixture was strongly agitated at 40° C. for 2 hours. Then, the roasted sesame residue was filtrated to obtain an extract. To the roasted sesame residue subjected to the filtration, 1.5 kg of 95% ethanol was added again. The mixture was strongly shaken at 40° C. for one hour, and then filtrated to obtain an extract. The total extract obtained by 2 cycles of filtration was concentrated, and 240 g of ethyl acetate and 80 g of water were added, followed by strongly shaking at 45° C. for 1 hour. After shaking, the water phase was removed, and 40 g of propylene glycol monooleate was added to the ethyl acetate phase. The ethyl acetate was evaporated to yield 58 g of roasted sesame residue extract 1 (18 g of roasted sesame residue extract in real terms because the extract contained 40 g of propylene glycol monooleate).

(2) Roasted Sesame Residue Extract 2

To 1.0 kg of roasted sesame residue was added 2.0 kg of 95% ethanol, and the mixture was strongly agitated at 40° C. for 2 hours. Then, the roasted sesame residue was filtrated to obtain an extract. To the roasted sesame residue subjected to the filtration, 1.5 kg of 95% ethanol was added again. The mixture was strongly shaken at 40° C. for one hour, and then filtrated to obtain an extract. To the total extract obtained by 2 cycles of filtration was added 40 g of propylene glycol monooleate. Then, the 95% ethanol was evaporated to yield 50 g of roasted sesame residue extract (10 g of roasted sesame residue extract in real terms because the extract contained 40 g of propylene glycol monooleate).

(3) Roasted Sesame Residue Extract 3

To 200 g of roasted sesame residue was added 300 mL of 95% ethanol, and the mixture was strongly shaken at 40° C. for 2 hours. Then, the roasted sesame residue was filtrated to obtain an extract. To the roasted sesame residue subjected to the filtration, 300 mL of 95% ethanol was added again. Then, the mixture was strongly agitated at 40° C. for 2 hours, and then filtrated to obtain an extract. The total extract obtained by 2 cycles of filtration was concentrated. Then, 150 mL of ethyl acetate and 50 mL of water were added, and the mixture was strongly agitated at room temperature for one hour. After the agitation, the water phase was removed, and further ethyl acetate was evaporated to yield 9.0 g of roasted sesame residue extract.

Roasted sesame residue extract 1 was subjected to a measurement by high-performance liquid chromatography with an electrochemical detector. The measurement was performed under the following conditions. The chart was shown in FIG. 6. Since the peaks were detected by the electrochemical detector, all the substances represented by the peaks have antioxidant properties. Thus, it is shown that the roasted sesame residue contains many antioxidative components, including sesamol and pinoresinol.

Measurement Conditions

Column: TSK-gel ODS-80Ts 4.6×150 mm

Eluant:
    0-5 min., methanol:water (containing 2% of 1 M ammonium acetate buffer (pH 4.4))=40:60
    10-17 min., methanol:water (containing 2% of 1 M ammonium acetate buffer (pH 4.4))=70:30
    22-40 min., methanol:water (containing 2% of 1 M ammonium acetate buffer (pH 4.4)) =100:0

Flow rate: 1.0 mL/min.

Column temperature: 35° C.

Sample concentration: 10-12 mg/mL

Sample solvent: methanol:ethanol:hexane =5:4:1

Injection volume: 10 μIL

Electrode 1 (reduction potential): −1 V

Electrode 2 (oxidation potential): 500 mV

Range: 20 μA

Samples were prepared by adding the following antioxidant preparations separately to refined fish oil (containing 0.5% by weight of δ-tocopherol).

roasted sesame residue extract 1 (1.0% by weight)+ascorbyl palmitate (0.05% by weight)
    roasted sesame residue extract 1 (1.0% by weight)+ascorbyl palmitate (0.1% by weight)
    roasted sesame residue extract 1 (1.0% by weight) alone
    ascorbyl palmitate (0.1% by weight) alone
    roasted sesame residue extract 2 (1.0% by weight)+ascorbyl palmitate (0.1% by weight)
    roasted sesame residue extract 3 (1.0% by weight)+ascorbyl palmitate (0.1% by weight)

Figure 7:
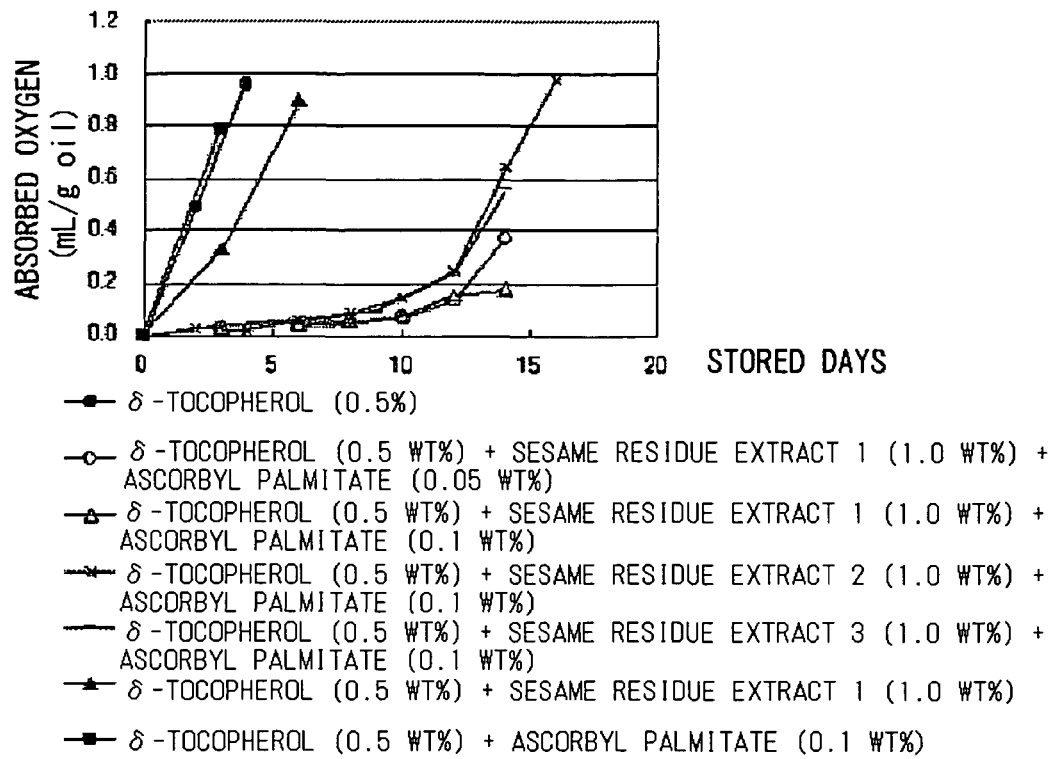
FIG. 7 shows changes with time in the amount of oxygen absorbed by samples of Example 6.

The samples were subjected to the same storage test as in Example 2. The results are shown in FIG. 7. It has been found that the roasted sesame residue extracts can reduce the amount of absorbed oxygen and increase the oxidative stability of the refined fish oil, by using them in combination with ascorbyl palmitate, as in the case of sesamol.

Example 7

<Test for Effect of Roasted Sesame Residue Extract+Ascorbyl Palmitate+δ-Tocopherol>

Figure 8:
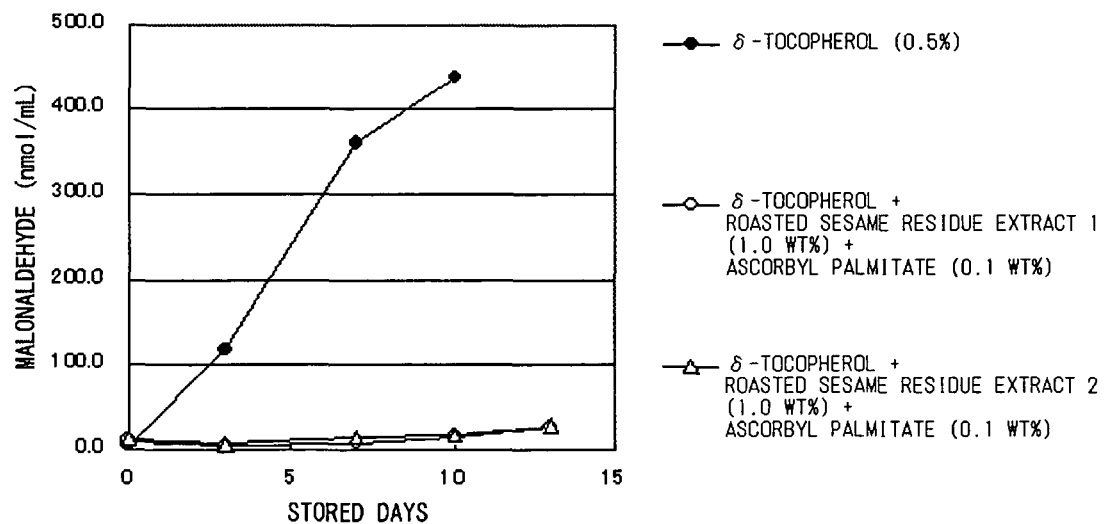
FIG. 8 shows changes with time in the malondialdehyde content in samples of Example 7.
Figure 9:
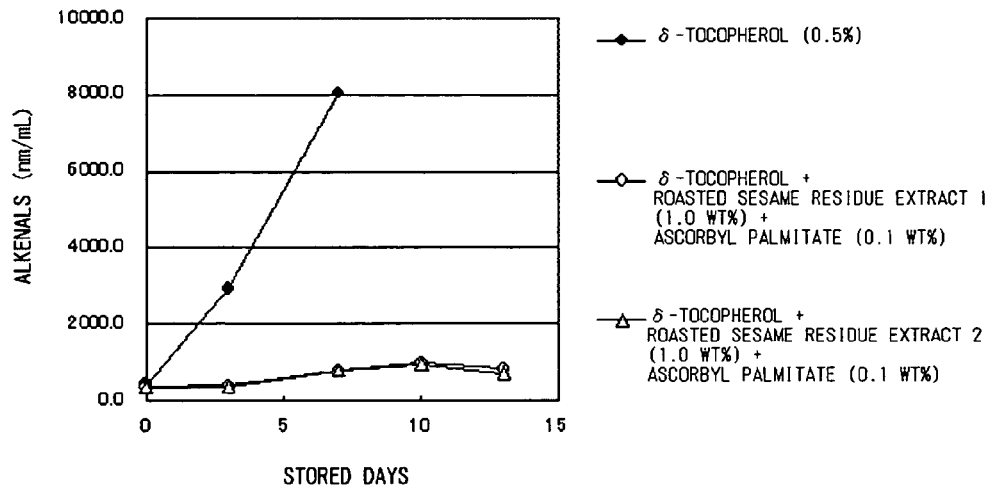
FIG. 9 shows changes with time in the alkenal content in samples of Example 7.

Samples were prepared by separately adding antioxidant preparations of Example 6: roasted sesame residue extract 1 (1.0% by weight)+ascorbyl palmitate (0.1% by weight); and roasted sesame residue extract 2 (1.0% by weight)+ascorbyl palmitate (0.1% by weight). In 20 mL brown bottles were placed 10 mL of the samples separately. Each mixture was stored at 60° C. with the bottle open, and changes in concentration of malondialdehyde and alkenals were measured during storage with SafTest produced by Saftest Inc. The results are shown in FIGS. 8 and 9. These figures show that by adding a roasted sesame residue extract and ascorbyl palmitate to refined fish oil, the generation of malondialdehyde and alkenals resulting from oxidation decomposition of fish oil, which are odorants of deteriorated fish oil, can be highly suppressed and thus the fish oil can be stabilized.

Example 8

Sesaminol obtained from roasted sesame residue extract 3 with a silica gel open column ODS-HPLC was used instead of the sesamol of Example 1. As a result, the same effect was produced.

Example 9

Pinoresinol obtained from roasted sesame residue extract 3 with a silica gel open column ODS-HPLC was used instead of the sesamol of Example 1. As a result, the same effect was produced.

Example 10

2,3-Di(4'-hydroxy-3'-methoxybenzyl)-2-buten-4-olide obtained from roasted sesame residue extract 3 with a silica gel open column ODS-HPLC was used instead of the sesamol of Example 1. As a result, the same effect was produced.

Example 11

<Test for Effect of Excessive Amount of Ascorbic Acid Ester>

The following antioxidant preparations were added separately to refined fish oil (containing 0.5% by weight of δ-tocopherol) to prepare samples.
  sesamol (0.5%)+ascorbyl palmitate (0.1%)
  sesamol (1.0%)+ascorbyl palmitate (0.1%)

After 4 mL of the samples were placed separately in respective 30 mL brown bottles and hermetically sealed with septums, the samples were stored at 60° C. The concentration of oxygen during storage was measured by gas chromatography, and thus the amount of oxygen reacted with (absorbed by) the oil was calculated. Also, the remaining antioxidant contents were analyzed by HPLC with an electrochemical detector.

Figure 10:
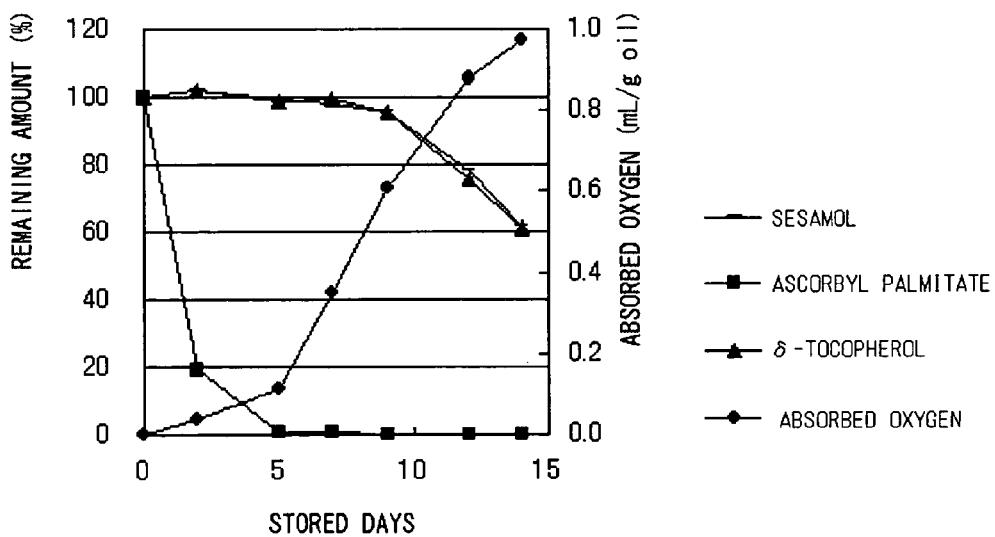
FIG. 10 shows changes with time in the amounts of oxygen absorbed by a sample (sesamol, 0.5%) and the remaining amounts of antioxidants in Example 11.
Figure 11:
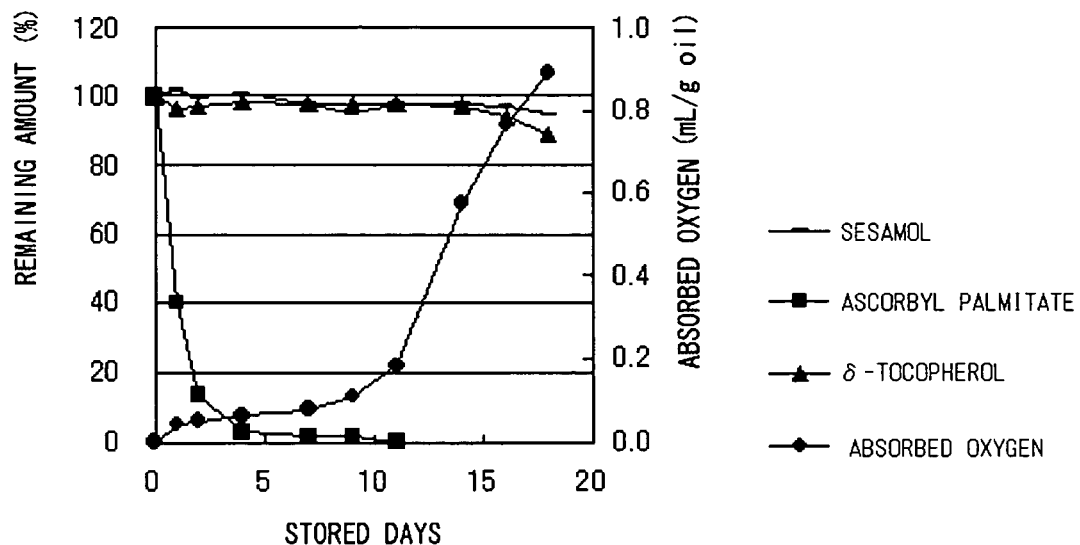
FIG. 11 shows changes with time in the amounts of oxygen absorbed by a sample (sesamol, 1.0%) and the remaining amounts of antioxidants in Example 11.
Figure 12:
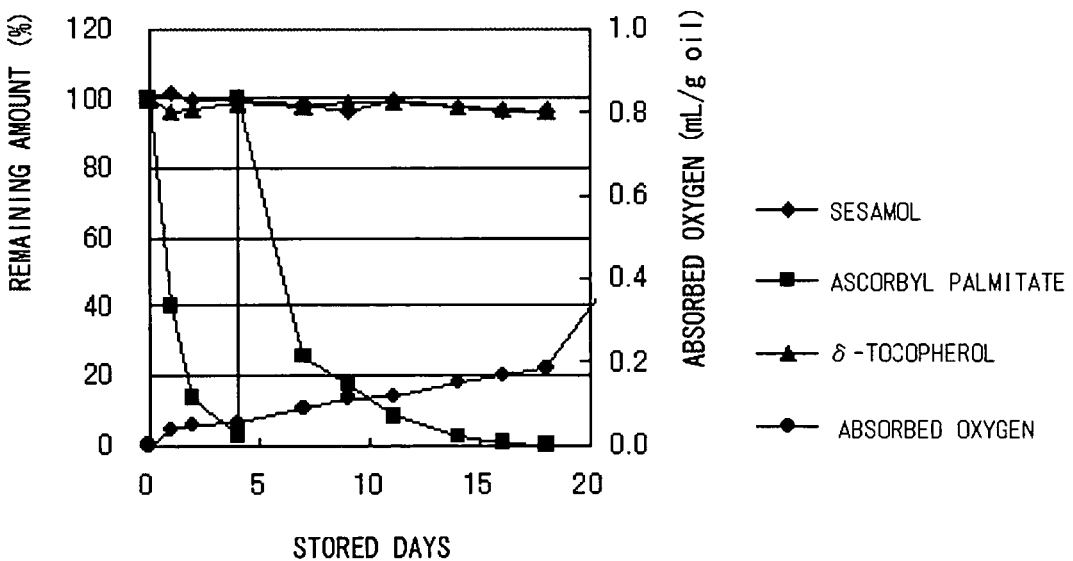
FIG. 12 shows changes with time in the amounts of oxygen absorbed by samples and the remaining amounts of antioxidants in the case where ascorbyl palmitate was added after 4 days in Example 11.

The results are shown in FIGS. 10 and 11. The figures show that, in either case, ascorbyl palmitate was consumed (oxidized) to be lost first, and then the refined fish oil, δ-tocopherol, and sesamol simultaneously started oxidizing. It is therefore assumed that ascorbyl palmitate plays an important role when the antioxidant preparation contains δ-tocopherol, sesamol, and ascorbyl palmitate. In order to confirm this assumption, 0.1% of ascorbyl palmitate was further added to the same system as in FIG. 11 on day four. The results are shown in FIG. 12. FIG. 11 shows that the oil was not oxidized until ascorbyl palmitate was consumed (around day ten); FIG. 12, in which ascorbyl palmitate was added on day four, shows that oxidation of the oil was continuously suppressed even after day ten.

Thus, it has been shown that it is important that ascorbyl palmitate is present in the antioxidant system of the present invention.

Example 12

<Tests for Effect on Eicosapentaenoic Acid Ethyl Ester of the Present Invention, and for Effect of Excessive Amount of Ascorbyl Palmitate>

Samples were prepared by adding the following antioxidant preparations separately to eicosapentaenoic acid ethyl ester with a purity of 99% (containing 0.2% of α-tocopherol)
  sesamol (1.0%)+ascorbyl palmitate (0.1%)
  sesamol (1.0%)+ascorbyl palmitate (0.5%)

Each sample was stored at 60° C., and the peroxide value (PV) was measured.

Figure 13:
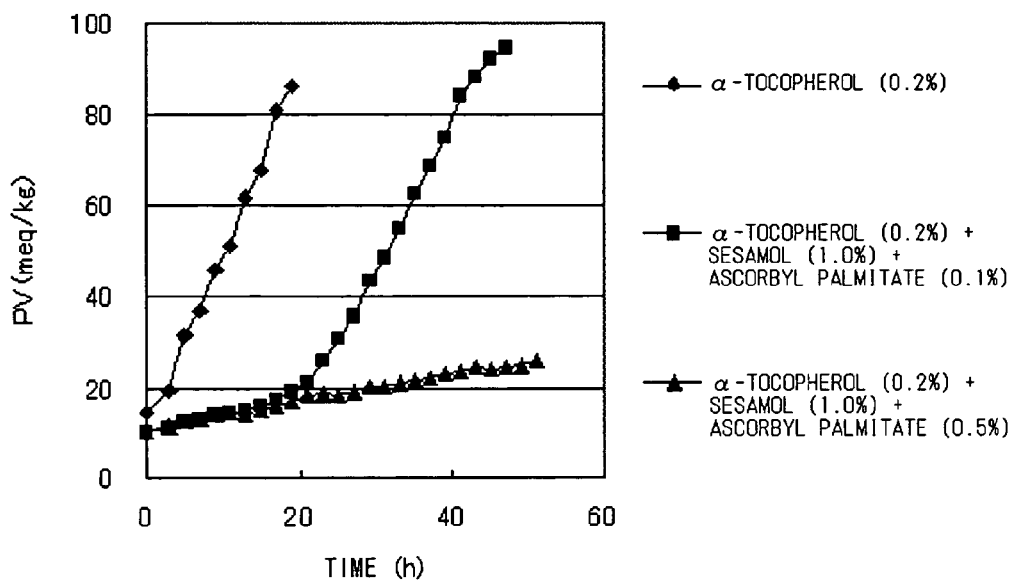
FIG. 13 shows changes with time in the PV of samples of Example 12.

The results are shown in FIG. 13. The antioxidant property of the antioxidant preparation containing an excessive amount of ascorbyl palmitate (0.5%) was maintained in comparison with that of the antioxidant preparation containing a soluble amount of ascorbyl palmitate (0.1%).

Example 13

<Comparison with Antioxidant (t-Butylhydroxytoluene (BHT)) Generally Used in External Preparations>

The antioxidant preparation of the present invention was compared with t-butylhydroxytoluene (BHT), which is an antioxidant generally used. Samples were prepared by adding 0.5%, 1.5%, or 10.0% of BHT, or 1.0% of sesamol and 0.5% of ascorbyl palmitate to refined fish oil (sardine oil) containing 0.5% of δ-tocopherol. To 30 mL brown bottles, 4 mL of the samples were placed separately. The bottles were hermetically sealed with septums and stored at 60° C. The oxygen concentration in the headspace was measured with time by gas chromatography and thus the amount of oxygen reacted with (absorbed by) the oil was calculated.

Results

Figure 14:
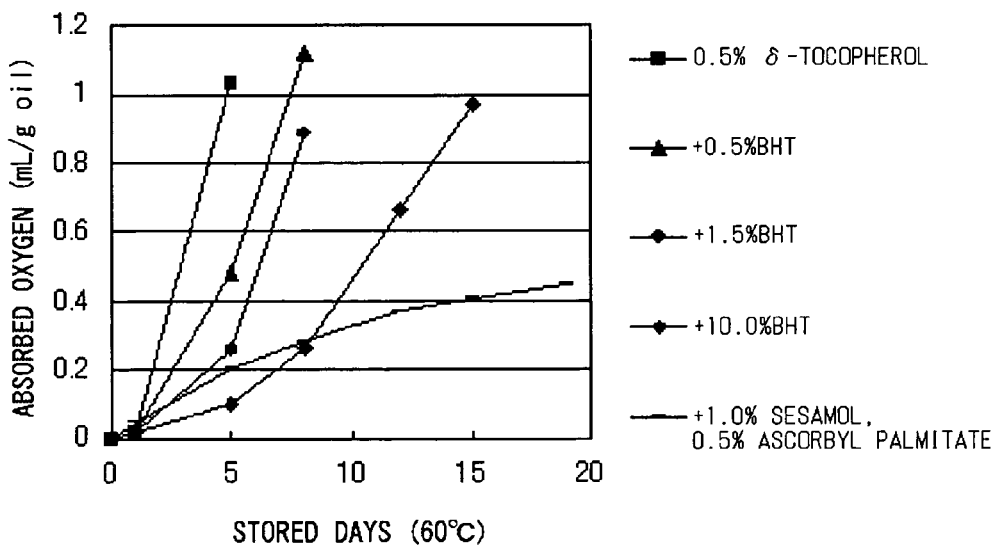
FIG. 14 shows comparison in antioxidant property between BHT and the antioxidant preparation according to the present invention.

FIG. 14 shows the comparison of the antioxidant properties between BHT and the antioxidant preparation of the present invention. The results show that the antioxidant preparation of the present invention exhibited higher antioxidant property than the same amount (1.5%) of BHT as the total amounts of the antioxidants in the antioxidant preparation of the present invention, and also than a much larger amount (10.0%) of BHT.

INDUSTRIAL APPLICABILITY

The present invention can provide oils and fats having oxidative stability far superior to known oils and fats containing a polyunsaturated fatty acid. Consequently, when a polyunsaturated fatty acid is added to food, medical drugs, and the like for health promotion, such products can be easily produced and preserved. Also, the types of food to which the composition is added and the polyunsaturated fatty acid content can be easily increased. Specifically, general-purpose refined fish oil containing EPA and DHA can be provided for health food or the like.

The invention claimed is:

1. A composition having oxidative stability comprising:
   polyunsaturated fatty acid or its salt or ester,
   an antioxidative sesame component which is purified from sesame or synthesized, and
   ascorbic acid or an ascorbyl fatty acid ester,
   wherein said antioxidative sesame component is in a range of 0.5-2.0%, and
   an amount of ascorbic acid or an ascorbyl fatty acid ester is 0.01% or more, which is effective for increasing oxidative stability.

2. A composition according to claim 1, wherein the poly unsaturated fatty acid contains at least one of eicosapentaenoic acid and docosahexaenoic acid.

3. A composition according to claim 1, wherein the ester of the poly unsaturated fatty acid is a triglyceride containing the poly unsaturated fatty acid as a constituent, or a lower alcohol ester of the poly unsaturated fatty acid.

4. A composition according to claim 1, wherein the ester of the poly unsaturated fatty acid is added in a form of refined fish oil.

5. A composition according to claim 1, wherein the antioxidative sesame component is at least one of the substances represented by peaks detected by high-performance liquid chromatography using an electrochemical detector at elution times of about 2.66, 3.40, 3.84, 4.57, 4.98, 5.82, 7.00, 8.67, 9.84, 11.24, 12.29, 12.49, 13.36, 14.04, 14.32, 14.74, 15.22, 15.60, 15.82, 16.34, 16.98, 18.10, 18.43, and 34.91 minutes.

6. A composition according to claim 1, wherein the antioxidative sesame component is extracted from sesame, sesame oil, or sesame residue, using a solvent, a lipid, or an emulsifier singly or in combination.

7. A composition according to claim 1, wherein the antioxidative sesame component is at least one selected from the group consisting of sesamol, sesaminol, episesaminol, pinoresinol, epipinoresinol, syringaresinol, samine, sesamolinol, and 2,3-di(4'-hydroxy-3'-methoxybenzyl)-2-buten-4-olide.

8. A composition according to claim 1, wherein the antioxidative sesame component is sesamol.

9. A composition according to claim 1, wherein the antioxidative sesame component is extracted from sesame residue.

10. A composition according to claim 9, wherein the antioxidative sesame component extracted from sesame residue is extraction using a solvent, a lipid, or an emulsifier singly or in combination.

11. A composition according to claim 1, wherein the ascorbyl fatty acid ester contains ascorbyl palmitate or ascorbyl stearate.

12. A composition according to claim 1, wherein a portion of the ascorbic acid or the ascorbyl fatty acid ester is undissolved in the poly unsaturated fatty acid or its salt or ester.

13. A composition according to claim 12, wherein the excessive amount of the ascorbic acid is in a powder or solid form.

14. A composition according to claim 1, further comprising tocopherol.

15. A composition as set forth in claim 1, wherein the composition is contained in a food.

16. A composition as set forth in claim 1, wherein the composition is contained in a powdered oil or fat.

17. A composition as set forth in claim 1, wherein the composition is contained in a powdered baby milk.

18. A composition as set forth in claim 1, wherein the composition is contained in a health food.

19. A composition having oxidative stability according to claim 1, wherein said antioxidative sesame component is sesamol, and wherein said sesamol is contained in a range of 0.5-1%.

* * * * *

UNITED STATES PATENT AND TRADEMARK OFFICE
CERTIFICATE OF CORRECTION

PATENT NO.         : 8,722,104 B2
APPLICATION NO.    : 10/535413
DATED              : May 13, 2014
INVENTOR(S)        : Doisaki et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1128 days.

Signed and Sealed this

Twenty-ninth Day of September, 2015

Michelle K. Lee
*Director of the United States Patent and Trademark Office*